US007246068B2

(12) United States Patent
Thomas, Jr.

(10) Patent No.: US 7,246,068 B2
(45) Date of Patent: Jul. 17, 2007

(54) COMPUTERIZED SYSTEM FOR COMBINING INSURANCE COMPANY AND CREDIT CARD TRANSACTIONS

(76) Inventor: James C. Thomas, Jr., 1005 Championship Way, Las Vegas, NV (US) 89134

( * ) Notice: Subject to any disclaimer, the term of this patent is extended or adjusted under 35 U.S.C. 154(b) by 40 days.

(21) Appl. No.: 09/927,296

(22) Filed: Aug. 10, 2001

(65) Prior Publication Data

US 2002/0138309 A1 Sep. 26, 2002

Related U.S. Application Data

(60) Provisional application No. 60/278,290, filed on Mar. 23, 2001.

(51) Int. Cl.
*G06Q 10/00* (2006.01)
(52) U.S. Cl. ............................................. 705/2; 705/26
(58) Field of Classification Search ................ 705/2, 705/26
See application file for complete search history.

(56) References Cited

U.S. PATENT DOCUMENTS

| | | | | |
|---|---|---|---|---|
| 5,025,372 | A | | 6/1991 | Burton et al. ................ 364/406 |
| 5,301,105 | A | * | 4/1994 | Cummings, Jr. ............... 705/2 |
| 5,705,798 | A | | 1/1998 | Tarbox ........................ 235/379 |
| 5,787,404 | A | | 7/1998 | Fernandez-Holmann ..... 705/35 |
| 5,806,045 | A | | 9/1998 | Biorge et al. ................. 705/14 |
| 5,850,217 | A | * | 12/1998 | Cole ........................... 715/700 |
| 5,884,271 | A | | 3/1999 | Pitroda .......................... 705/1 |
| 5,930,759 | A | | 7/1999 | Moore et al. |
| 5,945,653 | A | | 8/1999 | Walker et al. .............. 235/380 |
| 5,970,478 | A | | 10/1999 | Walker et al. ................. 705/35 |
| 5,970,480 | A | | 10/1999 | Kalina .......................... 705/37 |
| 6,105,865 | A | | 8/2000 | Hardesty ................... 235/380 |
| 6,108,641 | A | | 8/2000 | Kenna et al. ................. 705/35 |
| 6,151,586 | A | | 11/2000 | Brown ......................... 705/14 |
| 6,222,914 | B1 | | 4/2001 | McMullin ................... 379/144 |
| 6,386,444 | B1 | * | 5/2002 | Sullivan ..................... 235/379 |
| 2001/0014868 | A1 | | 8/2001 | Herz et al. |
| 2002/0029157 | A1 | | 3/2002 | Marchosky |

(Continued)

OTHER PUBLICATIONS

IDX Takes the Lead in Healthcare Billing; Integrated Software Simplifies Patient Payments; PR Newswire, Feb. 18, 1997; Newswire Association, Inc..*

(Continued)

*Primary Examiner*—Elaine Gort
(74) *Attorney, Agent, or Firm*—Christie, Parker & Hale, LLP.

(57) ABSTRACT

A method and apparatus for combining a credit card account with a medical services or insurance account. A client establishes a credit card account and links the credit card account to an insurance policy or medical services account. The client uses the credit card and generates rebates used to offset the cost of the insurance policy or make payments into the medical services account. The form of the rebate depends on the type of insurance policy or medical services account selected by the client. An interactive Web site is provided for creation, coordination, and monitoring of the linked credit card accounts and insurance policies. A client uses the interactive Web site to explore different insurance policies and the effects of using credit card rebates to offset the price of an insurance policy. The interactive Web site also provides services for the client to maintain and monitor the linked accounts.

5 Claims, 5 Drawing Sheets

U.S. PATENT DOCUMENTS

2002/0111832 A1    8/2002    Judge

OTHER PUBLICATIONS

Shop—The Card You Pick Can Save You Money; The Federal Reserve Board, Nov. 3, 1999; pp. 1-6.*
The Profitability of Credit Card Operations of Depository Institutions; The Federal Reserve Board; Jun. 1999, pp. 1-8.*
GMcard.com; May 2000; 2 pages; obtained from archive.org.*
"IDX Takes the Lead in Healthcare Billing; Integrated Software Simplifies Patient Payments," PR Newswire, 2 pages, Feb. 18, 1997.
"Phar-Mor and Personalmd.com Form Strategic Partnership to Provide Phar-Mor Customers with Online Access to Personalized Medical Records," PersonalMD Press Release, www.personalmd.com/press19_article.shtml, 3 Pages, Sep. 27, 1999.
"Personalmd.com and Healthaxis.com Partner to Offer Consumers Online Medical Records and Insurance Services," PersonalMD press Release, www.personalmd.com/press30_article.shtml, 4 Pages, Dec. 13, 1999.
"Personalmd.com and HealthAllies.com Partner to Offer Consomers Greater Control of Their Personal Health and Medical Bills," PersonalMD Press Release, www.personalmd.com/press26_article.shtml<http://www.personalmd.com/press26_article.shtml, 4 Pages, Jan. 4, 2000.
"Channelhealth Announces Availability of Web Portal to Link Physicians and Patients," ChannelHealth Press Release, http://ask.idx.com/corporateweb/press.nsf/, 2 Pages, Apr. 10, 2000.
International Preliminary Examination Report from the corresponding PCT Application No. PCT/US02/09156; May 23, 2003, 4 Pages.
Patent No. EP0717381, synopsis of patent application entitled System and Method for Processing Customized financial transaction card; publication date Jun. 19, 1996.
Patent No. 6,098,881; abstract of patent entitled Magnetic Stripe Card Verification System, date unknown.
Lucas, Copyright 1998 Faulkner & Gray article entitled "Credit Card Management"; Load Date: May 8, 1998
Ezpreapproval.com article entitled "Credit Cards That Offer Rewards" (date unknown).
Bankrate.com article entitled "Credit card bill promotions are good deals—for the issuer, not you" dated Feb. 7, 2000.
On-line article re "Halliburton Employees' Federal Credit Union" re various VISA cards. (date unknown).

* cited by examiner

COMPUTERIZED SYSTEM FOR COMBINING INSURANCE COMPANY AND CREDIT CARD TRANSACTIONS

CROSS-REFERENCE TO RELATED APPLICATION

The present application claims priority to U.S. Provisional Patent Application No. 60/278,290, filed Mar. 23, 2001, which is hereby incorporated by reference as if set forth in full herein.

TECHNICAL FIELD OF THE INVENTION

This invention relates generally to credit card systems and more specifically to the application of credit card rebates to pay for medical or insurance services.

BACKGROUND OF THE INVENTION

Credit cards providing rebates in the form of airline miles for purchases, cash back for purchases, or cash down payments for automobiles have been successful in attracting customers and enlarging the businesses of the credit card companies and the vendors aligned with the credit card companies. Credit card company clients are attracted to the credit cards offering rebates because a client receives a monetary incentive to use credit cards offering rebates. Credit card companies benefit from greater market share created by increased client interest in the credit cards offering rebates. Product and service vendors enjoy increased customer loyalty created by clients working towards increased rebates resulting in larger market share and less customer volatility. The system of credit card rebates pays for itself through customer loyalty, increased market stability, increased resource utilization, and economies of scale.

However, a recent article in a California paper indicated that 20% of all California residents do not have health insurance. National statistics are similar. In addition, only a small percentage of people own any type of life insurance, long term care insurance, or disability insurance in case they are disabled from performing the duties of their occupations.

Insurance companies and health care providers could benefit from an alliance with credit card companies to provide insurance benefits to clients using rebates generated from credit card purchases. The present invention provides a system to form such an alliance.

SUMMARY OF THE INVENTION

In one aspect of the invention, a method is provided for integrating credit card purchases with insurance premium payments. A client establishes a credit card account and links the credit card account to an insurance account. The client uses the credit card and generates rebates credited to the insurance account. The insurance account can be used to pay for purchases of different kinds of insurance policy premiums or pay for various services associated with an insurance policy.

In another aspect of the invention, an interactive management Web site is provided for creation, coordination, and monitoring of linked credit card accounts and insurance policies. A client uses the interactive Web site to explore different insurance policies and the effects of using credit card rebates to offset the price of an insurance policy. The interactive Web site also provides services for the client to maintain and monitor the linked accounts.

In another aspect of the invention, a system is provided for integrating credit card purchases with a medical services account. A client establishes a credit card account and links the credit card account to the medical services account. The client uses the credit card and generates rebates credited to the medical services account. The medical services account can be used to pay for purchases of different kinds of medical expenses.

BRIEF DESCRIPTION OF THE DRAWINGS

These and other features, aspects, and advantages of the present invention will become better understood with regard to the following descriptions and accompanying drawings where.

DETAILED DESCRIPTION OF THE INVENTION

A credit card system according to the present invention allows insurance companies to empower current and new customers with credit card rebates applied to health care benefits such as insurance policy premiums, policy upgrades, vouchers for health care services and products, health care spending accounts, etc.

In one embodiment of the present invention, insurance companies negotiate agreements with credit card companies with existing systems currently in place to provide rebates to the insurance companies' clients.

In another embodiment of the present invention, insurance companies develop their own credit cards.

Figure 1:
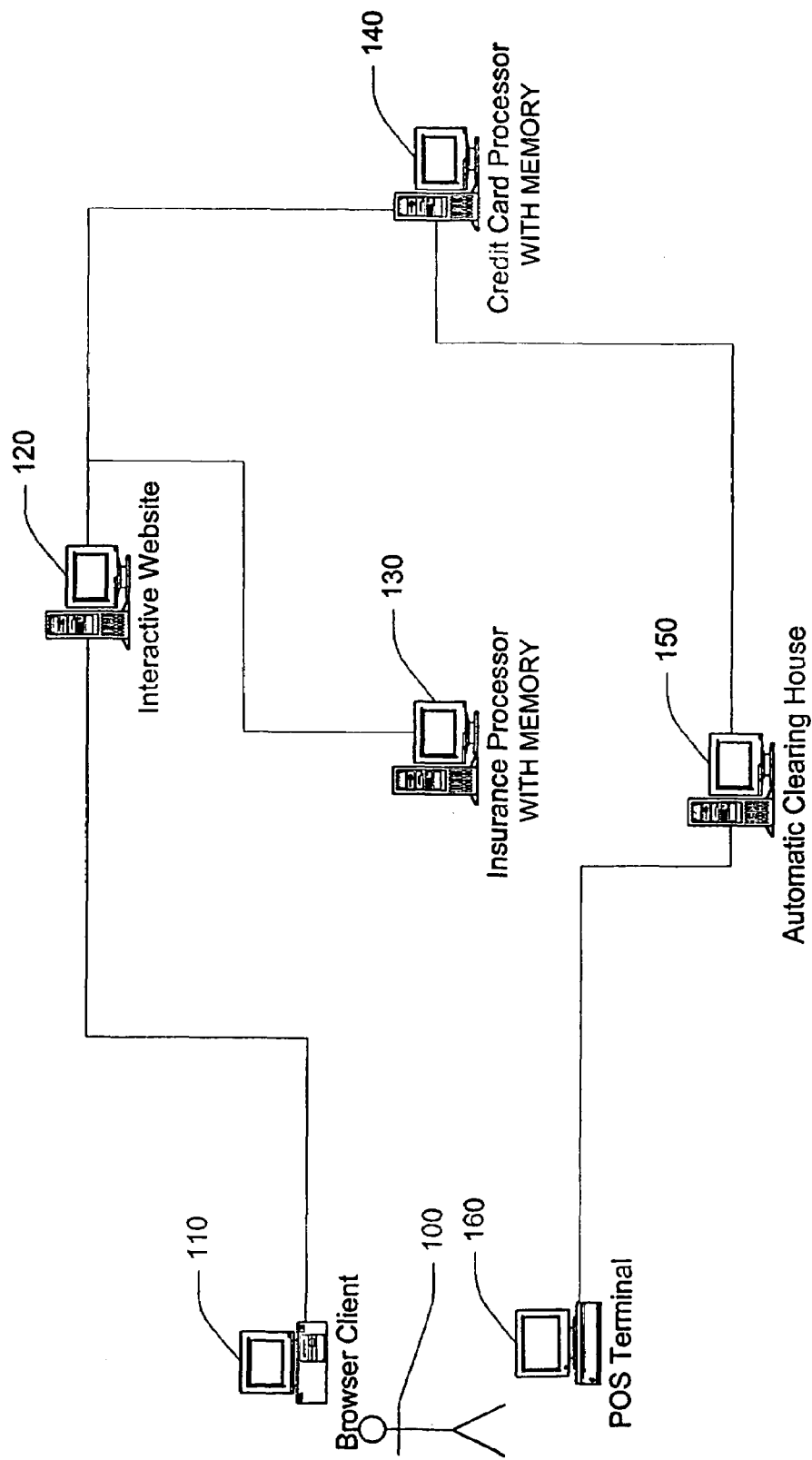
FIG. 1 is deployment diagram depicting components of an embodiment of a networked credit card and insurance billing system according to the present invention.

FIG. 1 is deployment diagram depicting components of an embodiment of a networked credit card and insurance billing system according to the present invention. An interactive Web site 120 is operably coupled to a plurality of browser clients as exemplified by browser client 110. The interactive Web site is also operably coupled to an insurance company's main processing system 130 and a credit card company's main processing system 140 via a communication network such as the Internet. The credit card company's main processing system is operably coupled to an Automatic Clearing House (ACH) 150 via a communications network. The ACH is operably coupled to a Point of Sale (POS) terminal 160.

The credit card company's main processing system 140 further includes a processor 142 operably coupled via a system bus 144 to a memory 146. The memory includes stored program instructions 148. The program instructions are used by the processor to implement the features of a credit card company's main processing system as described herein.

A client 100 uses the browser client to contact the interactive Web site and establish accounts on both the insurance company's main processing system and the credit card company's main processing system. The client uses the credit card at a retailer's POS terminal and the ACH clears the transaction. The ACH forwards the credit card transactions to the credit card company's main processing system and the client's rebates are calculated. The client's rebates are forwarded to the insurance company's main processing system where the rebates are processed into an award given to the client.

In another embodiment of a credit card system according to the present invention, an interactive Web site is hosted by a credit card company computer system. A client uses the Web site to establish a credit card account and links the credit card account to a health benefits account such as an insurance policy held with an insurance company.

In another embodiment of a credit card system according to the present invention, an interactive Web site is hosted by an insurance company. In this embodiment, the client establishes an account with the insurance company and then links the account with a credit card.

In another embodiment of a credit card system according to the present invention, the client creates linked accounts by communicating with the credit card and insurance company via telephone or the postal system in a conventional manner.

Figure 2:
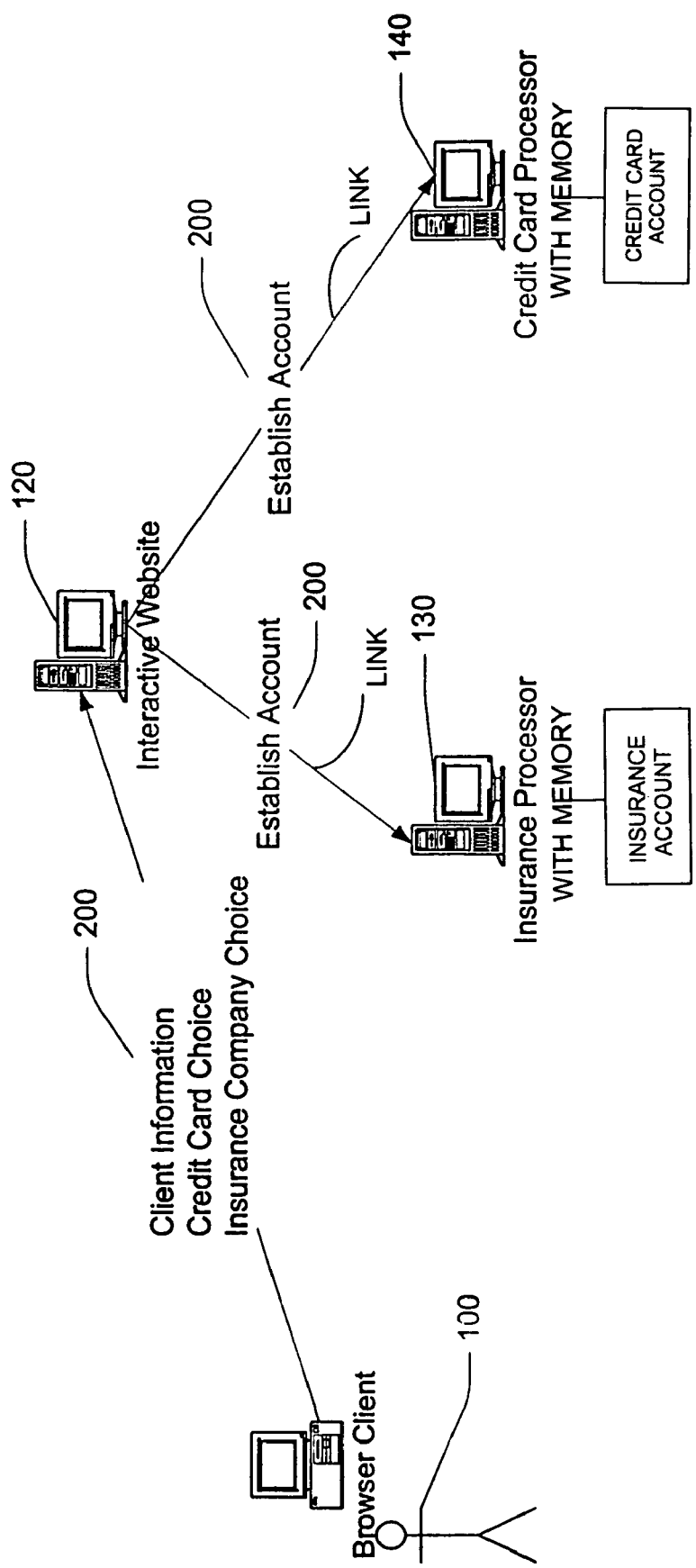
FIG. 2 is a collaboration diagram depicting an enrollment process according to an embodiment of the present invention.

FIG. 2 is a collaboration diagram depicting an enrollment process according to an embodiment of the present invention. A client 100 uses a browser client 110 to access an interactive Web site 120 via the Internet. The Web site serves a series of Web pages comprising a user interface allowing the client to enroll in a credit card rebate program. The client sends client information, a credit card choice, and an insurance policy choice 200 to the interactive Web site. The interactive Web site establishes an account 200 for the client on an insurance company's main processing system 130 and establishes a linked account 200 on the credit card company's main processing system 140.

The type of account established by the client with the insurance company may vary. The insurance company may sell health, whole life, term life, long term care, or disability policies to the client. Simultaneously, the client applies for a credit card with an existing credit card company. The client designates the type of policy to which a rebate applies.

Once the credit card account and the insurance account are linked, each client purchase using the credit card generates a rebate related to the purchase, e.g., equal to a percentage of the total purchase. On the next statement of the billing cycle, the insurance premium is reduced by the rebate amount.

In other embodiments of the present invention, different types of rebates apply depending on the type of insurance obtained by the client. In one embodiment, the rebate is applied to offset the premium payments on health or life insurance.

In another embodiment of the present invention, a client's insurance policy is upgraded to a policy with improved coverage. For example, the health insurance of a client who purchased an Health Maintenance Organization (HMO) policy is upgraded to a Preferred Provider Organization (PPO) policy.

In another embodiment of the present invention, the credit card rebates are used to fund a term or whole life insurance policy.

In another embodiment of the present invention, the credit card rebates are used to fund a long term care or disability insurance policy. For seniors on Medicare, Medicare "gap" insurance could be funded in the same manner.

In another embodiment of the present invention, rebates are provided to the client in the form of cash vouchers based on the amount of the client's purchases or the number of times the client uses the credit card. These cash vouchers are redeemable by the client at participating health service providers, such as for making co-payments to professionals or to purchase prescription drugs.

Figure 3:
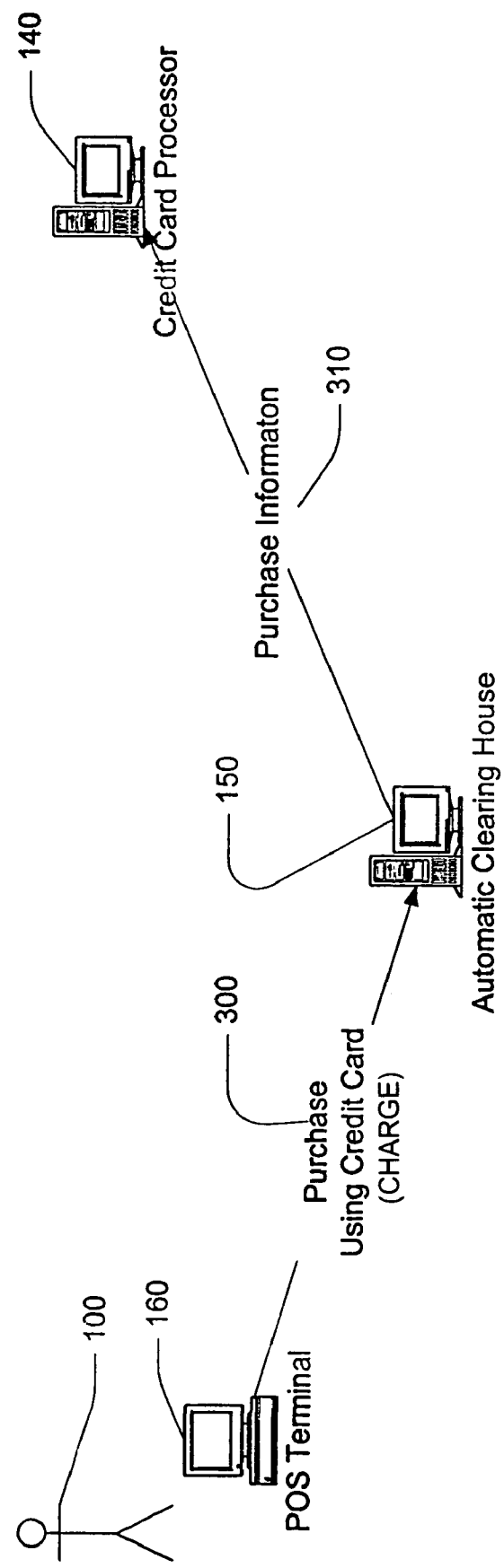
FIG. 3 is a collaboration diagram illustrating a client using a credit card to make purchases according to an embodiment of the present invention.

FIG. 3 is a collaboration diagram illustrating a client using a credit card to make purchases according to an embodiment of the present invention. An issued credit card is used like any conventional credit card. For example, a client 100 uses the credit card to make a purchase using a POS terminal 160 at a retail outlet. The POS terminal sends transaction information 300 to an ACH 150. The ACH clears the transaction and sends transaction information 310 to a credit card company's central credit card processing system 140.

Figure 4:
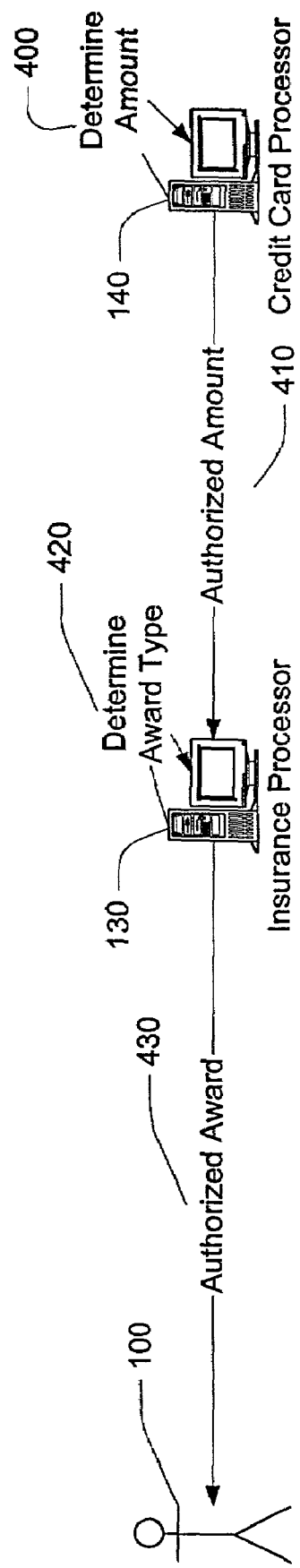
FIG. 4 is a collaboration diagram depicting a rebate form of an award being given to a client in an embodiment according to the present invention.

FIG. 4 is a collaboration diagram depicting a rebate form of an award being given to a client in one embodiment of the present invention. The credit card company's central computer system determines 400 the amount of rebate given to a client 100 based on the client's purchases. The amount of the rebate is sent to an insurance company's central computer system 130 where the type of award to be given is determined 420. As previously discussed, the type of award is dependent on the type of insurance account maintained by the client. The award is then given 430 to the client.

In another embodiment of the present invention, information is managed by a central computer system. This embodiment is useful in conglomerates where banking systems and insurance companies are owned by the same entity. In this embodiment, no money transfer occurs. The central computer system integrates the client's insurance account with a credit card account and the rebated amount is deducted from the appropriate insurance policy premium payments.

In cases where excellent health care is already provided by an employer, either life insurance, long term care insurance, or disability insurance is a desirable additional option for the client. In this case, the credit card system encourages the client to pursue additional insurance products such as life, long term care, or disability insurance.

In other cases, the credit card system allows the client to pay for elective procedures not covered under the client's existing insurance policies. Examples of elective procedures not normally covered by insurance policies are cosmetic surgeries and surgeries to correct vision defects that can be corrected using corrective lenses.

In another embodiment of the present invention, a client requests a credit card with debit card capacity such as a "smart card". All purchases are recorded and a percentage of the smart card purchases are rebated to the customer and deposited into a medical services account maintained with a central bank. The client uses the deposited rebates as an accessible "health bank". The "health bank" is accessed to its capacity for health care expenditures. These include: health care co-payments or deductibles paid to health care professionals such as doctors and dentists; prescription drug co-payments or purchases; and eyewear prescriptions or other durable medical equipment.

As previously stated, a central computer with appropriate custom software compiles the bank information each credit card client will accrue. Also the central computer debits the client's account with the client's desired transactions and transfers the funds out of the client's accrued bank amount for the appropriate health care transaction.

In one embodiment of the present invention, a debit stripe is applied to an insurance card, thus enabling direct access to a client's health bank. A client uses the insurance card to debit the client's health bank at the time of a health care expenditure.

In this embodiment, use of the insurance card includes a verification step to verify that the client has sufficient credit in the client's health bank to cover the health care services. If there is insufficient credit in the health bank, the health care bank can be linked to an alternative source of funds such as a banking account or credit card. The alternative source of funds is then used to cover the client's overdraft of the health bank.

In another embodiment of an insurance card with a debit stripe, the client can take advantage of the insurance company's superior economic position to receive discounted health care services. In this embodiment, the health care provider is not credited directly out of the client's health bank and instead bills the health bank for pre-negotiated discounted fees.

In another embodiment of the present invention, a separate card with debit capability is given to the client to promote instantaneous transfer of funds compiled in the bank. In this embodiment, the account is debited instantaneously extending the connection between the credit card company and the insurance company to a different segment of the health care population. Health care providers are brought into an association of preferred network providers. These providers provide a discount of their services to the clients. In exchange for the allegiance of the health care providers, the credit card company promotes the health care providers with advertising by the insurance company. Health care providers include medical and dental professionals, pharmacists, therapists, outpatient services, etc.

The extension of the business network allows the insurance company to extend itself thus increasing its potential clout within the health care industry. This allows better control of health care expenditures and better documentation, again via the central computer, by tracking the actual purchases and utilization of dollars spent for health care by the credit card system and dollars redeemed via the health care "bank account". Appropriate epidemiology of patient base with respect to regional and age differences are documented allowing better control of health care services.

In another embodiment of the present invention, the insurance company provides hardware and software to the health care profession preferred network for all transactions. This allows the client again to debit their "bank account" for immediate purchases of health care services.

In another embodiment of the present invention, an interactive Web site provides explanation of the insurance products and credit card integration.

In one embodiment of an interactive Web site according to the present invention, a client enters his/her credit card purchase totals over a period of time. The interactive Web site program calculates the rebate that the client will earn and provides the client with prices for health, life (term or whole), long term care insurance, or disability insurance. Thus, the client has access to information necessary to make decisions as to whether or not this is a proper route for the client to pursue.

In another embodiment of an interactive Web site according to the present invention, a client uses the interactive Web site to manage both the credit card account and the insurance account.

In one embodiment of the credit card system according to the present invention, insurance companies negotiate with employers to provide a health care insurance that might be more affordable for the insurance company and the employer if each employee takes and uses a credit card for a certain number of transactions per month. For example, the employer purchases health maintenance organization insurance for each and every employee, but by using the credit for either a certain dollar rebate amount or using it for a certain number of transactions per month, the employee gets an upgrade to a preferred provider insurance plan allowing access to different health care providers.

A credit card system according to the present invention may also be applied to other insurance products where deductibles or recurring premiums are used. For example, most insurance clients carry auto insurance policies with large deductibles in order to reduce the cost of the monthly premiums. However, most insurance clients fail to set aside the amount of the deductible in the insurance client's budget and are therefore unprepared when an accident occurs. Credit card rebates linked to a car insurance deductible account allow an insurance client to build up a deductible account in order to pay the deductible in case of an accident. The deductible account could also be used to pay regular car insurance premiums as well.

Homeowner's insurance policies share the same characteristics of deductibles and recurring premiums as car insurance. Most homeowners do not set budgets for the loss of a home because the loss of a home is typically a once in a lifetime event. In this case, linking a credit card to a deductible account allows an insurance client to painlessly build an account balance over a long period of time.

In another embodiment, homeowner insurance premiums are paid for out of the deductible account.

Figure 5:
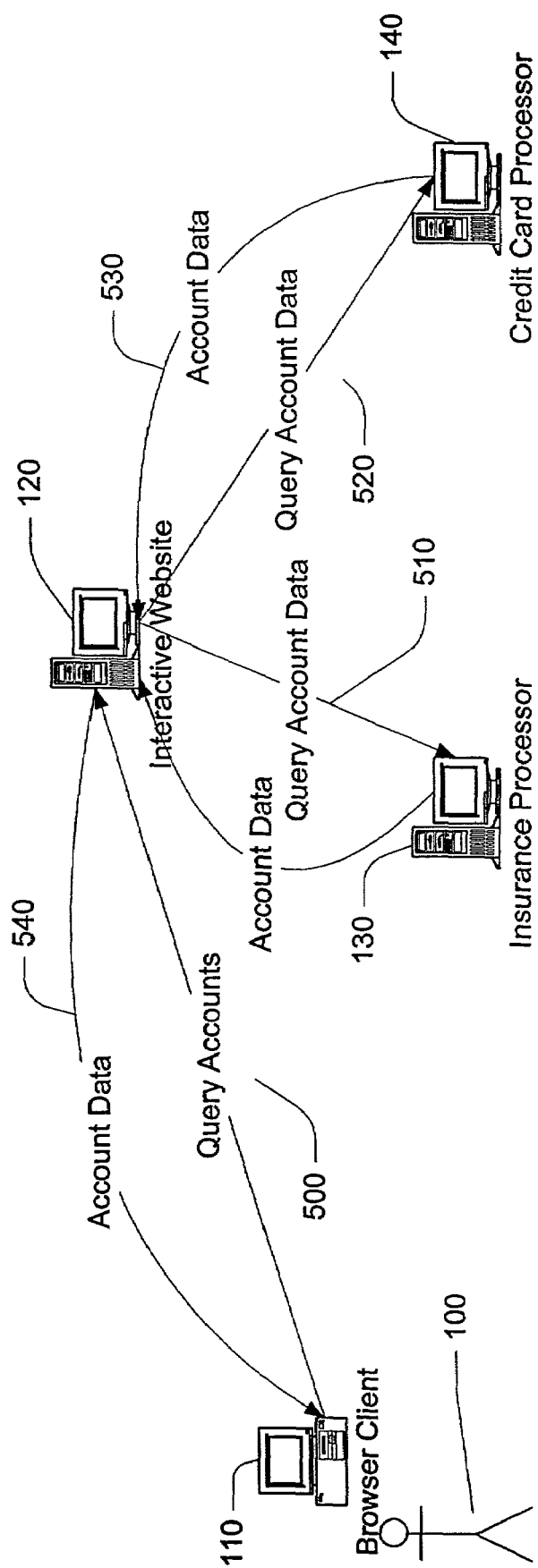
FIG. 5 is a collaboration diagram depicting interactions between a user and an exemplary account management Web site according to the present invention.

FIG. 5 is a collaboration diagram depicting interactions between a user and an exemplary account management Web site according to the present invention. An interactive Web site 120 is operably coupled to a plurality of browser clients as exemplified by browser client 110. The interactive Web site is also operably coupled to an insurance company's main processing system 130 and a credit card company's main processing system 140 via a communication network such as the Internet.

A client 100 uses the browser client to contact the interactive Web site and transmit an account query 500 to the interactive Web site. The interactive Web site in turn generates an insurance account query 510 and transmits the insurance account query to the insurance processor. The insurance processor responds to the insurance account query by transmitting insurance account data 512 to the interactive Web site. The interactive Web site generates an credit card account query 520 and transmits the credit card account query to the credit card processor. The credit card processor generates credit card account data 530 and transmits the credit card account data to the interactive Web site in response to the credit card account query.

The interactive Web site receives the insurance account data and credit card account data and generates an account report 540 from the two data sets. The account report is transmitted by the interactive Web site to the browser client where the account report is displayed. In this manner, the client can keep track of both the client's credit card purchases and expenses as well as the client's insurance policies.

Although this invention has been described in certain specific embodiments, many additional modifications and variations would be apparent to those skilled in the art. For example, the embodiments described above could be modified so that credit card purchases by one party could yield a benefit to another party. Thus, a son or daughter could use rebates earned with credit card purchases toward the premiums for long-term extended care coverage for their parents.

It is therefore to be understood that this invention may be practiced otherwise than as specifically described. Thus, the present embodiments of the invention should be considered in all respects as illustrative and not restrictive, the scope of the invention to be determined by claims supported by this application and the claim's equivalents rather than the foregoing description.

What is claimed is:

1. A method for providing rebates for charges made to a credit card as payments for amounts due on an insurance account, the method comprising:
    providing a web site displaying a plurality of insurance policies to which the rebates may be applied;
    receiving at the website, a user selection of at least one of the displayed plurality of insurance policies for applying the rebates;
    identifying, at the website, an insurance account associated with the user selected insurance policy;
    identifying, at the web site, a credit card account;
    linking the insurance account with the credit card account;
    calculating a rebate amount based on a purchase amount charged to the credit card account using an associated credit card;
    electronically transmitting the rebate amount to a remote processing system associated with the insurance account; and
    applying, by the remote processing system, the rebate amount to the insurance account.

2. The method of claim 1, wherein the remote processing system is accessed over a wide area data communications network.

3. The method of claim 1, wherein the rebate amount is a percentage of a purchase amount charged to the credit card account.

4. The method of claim 1 further comprising:
    automatically identifying an amount due on the insurance account; and
    automatically applying the rebate amount to the amount due on the insurance account and reducing the amount due.

5. A method for providing rebates for charges made to a credit card for making payments for medical expenses, the method comprising:
    calculating a rebate amount based on a purchase amount charged to a credit card account using an associated credit card;
    identifying a medical services account associated with the credit card account;
    transferring funds associated with the rebate amount to the identified medical services account;
    receiving information on a medical expenditure associated with the medical services account;
    automatically transferring funds out of the medical services account based on the medical expenditure;
    verifying an amount of existing funds in the medical services account;
    linking the medical services account to a second account;
    detecting insufficient funds in the medical services account; and
    transferring the detected insufficient funds amount out of the second account.

* * * * *